United States Patent
Sinko et al.

(10) Patent No.: US 7,846,893 B2
(45) Date of Patent: Dec. 7, 2010

(54) DRUG-POLYMER CONJUGATES COUPLED TO A PEPTIDIC CARRIER

(75) Inventors: Patrick J. Sinko, Lebanon, NJ (US); Stanley Stein, East Brunswick, NJ (US); Simi Gunaseelan, Highland Park, NJ (US); Shahriar Pooyan, Mount Kisco, NY (US); Li Wan, Randolph, NJ (US); Xiaoping Zhang, Edison, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 240 days.

(21) Appl. No.: 11/816,317

(22) PCT Filed: Feb. 16, 2006

(86) PCT No.: PCT/US2006/005729

§ 371 (c)(1),
(2), (4) Date: Oct. 10, 2007

(87) PCT Pub. No.: WO2006/089156

PCT Pub. Date: Aug. 24, 2006

(65) Prior Publication Data

US 2008/0188399 A1    Aug. 7, 2008

Related U.S. Application Data

(60) Provisional application No. 60/653,125, filed on Feb. 16, 2005.

(51) Int. Cl.
*A61K 38/00* (2006.01)
*A61K 38/06* (2006.01)
*A61K 38/08* (2006.01)
*A01N 25/34* (2006.01)

(52) U.S. Cl. .............................. 514/2; 514/16; 514/18; 530/300; 530/329; 530/331; 424/404

(58) Field of Classification Search ...................... None
See application file for complete search history.

(56) References Cited

U.S. PATENT DOCUMENTS

2003/0091640 A1 * 5/2003 Ramanathan et al. ....... 424/486

OTHER PUBLICATIONS

Pooyan, 2002, Bioconjugate Chemistry, 13, 216-223.*
Law, Journal of pharmaceutical sciences, (Aug. 2001) vol. 90, No. 8, pp. 1015-1025.*
Duncan, R., "Drug-Polymer Conjugates: Potential for Improved Chemotherapy", Anti-Cancer Drug, Jun. 1992, vol. 3. pp. 175-210.
Hallbrink, M., "Cargo Delivery Kinetics of Cell-Penetrating Peptides", Biochimica et Biophysica Acta, Dec. 2001, vol. 1515. pp. 101-109.

* cited by examiner

*Primary Examiner*—Cecilia Tsang
*Assistant Examiner*—Satyanarayana R Gudibande
(74) *Attorney, Agent, or Firm*—Fox Rothschild LLP; Peter J. Butch, III; Shahnam Sharareh

(57) ABSTRACT

Monodisperse macromolecular conjugate compositions of a peptidic carrier irreversibly or reversibly conjugated with one or more effectors and one or more therapeutic agents, wherein at least one effector or therapeutic agent is attached to a pendant reactive group on said peptidic carrier via a water-soluble polymer. Monodispersity is obtained through the use of orthogonal and separate conjugation reactions.

42 Claims, 2 Drawing Sheets

SEQUENCE LISTING

```
<160> NUMBER OF SEQ ID NOS: 7

<210> SEQ ID NO 1
<211> LENGTH: 3
<212> TYPE: PRT
<213> ORGANISM: Artificial
<220> FEATURE:
<223> OTHER INFORMATION: artificial peptidic carrier
<220> FEATURE:
<221> NAME/KEY: MISC_FEATURE
<222> LOCATION: (2)..(2)
<223> OTHER INFORMATION: bAla

<400> SEQUENCE: 1

Cys Ala Lys
1

<210> SEQ ID NO 2
<211> LENGTH: 13
<212> TYPE: PRT
<213> ORGANISM: Artificial
<220> FEATURE:
<223> OTHER INFORMATION: artificial peptidic carrier
<220> FEATURE:
<221> NAME/KEY: MISC_FEATURE
<222> LOCATION: (2)..(2)
<223> OTHER INFORMATION: bAla
<220> FEATURE:
<221> NAME/KEY: MISC_FEATURE
<222> LOCATION: (4)..(4)
<223> OTHER INFORMATION: bAla
<220> FEATURE:
<221> NAME/KEY: MISC_FEATURE
<222> LOCATION: (6)..(6)
<223> OTHER INFORMATION: bAla
<220> FEATURE:
<221> NAME/KEY: MISC_FEATURE
<222> LOCATION: (8)..(8)
<223> OTHER INFORMATION: bAla
<220> FEATURE:
<221> NAME/KEY: MISC_FEATURE
<222> LOCATION: (10)..(10)
<223> OTHER INFORMATION: bAla
<220> FEATURE:
<221> NAME/KEY: MISC_FEATURE
<222> LOCATION: (12)..(12)
<223> OTHER INFORMATION: bAla

<400> SEQUENCE: 2

Cys Ala Lys Ala Lys Ala Lys Ala Lys Ala Lys Ala Lys
1               5                   10
```

```
<210> SEQ ID NO 3
<211> LENGTH: 7
<212> TYPE: PRT
<213> ORGANISM: Artificial
<220> FEATURE:
<223> OTHER INFORMATION: artificial peptidic carrier
<220> FEATURE:
<221> NAME/KEY: MISC_FEATURE
<222> LOCATION: (1)..(1)
<223> OTHER INFORMATION: optionally, Acetyl-
<220> FEATURE:
<221> NAME/KEY: MISC_FEATURE
<222> LOCATION: (2)..(3)
<223> OTHER INFORMATION: bAla
<220> FEATURE:
<221> NAME/KEY: MISC_FEATURE
<222> LOCATION: (5)..(6)
<223> OTHER INFORMATION: bAla
<220> FEATURE:
<221> NAME/KEY: MISC_FEATURE
<222> LOCATION: (7)..(7)
<223> OTHER INFORMATION: -Amide

<400> SEQUENCE: 3

Cys Ala Ala Lys Ala Ala Lys
1               5

<210> SEQ ID NO 4
<211> LENGTH: 13
<212> TYPE: PRT
<213> ORGANISM: Artificial
<220> FEATURE:
<223> OTHER INFORMATION: artificial peptidic carrier
<220> FEATURE:
<221> NAME/KEY: MISC_FEATURE
<222> LOCATION: (1)..(1)
<223> OTHER INFORMATION: Acetyl-
<220> FEATURE:
<221> NAME/KEY: MISC_FEATURE
<222> LOCATION: (2)..(3)
<223> OTHER INFORMATION: bAla
<220> FEATURE:
<221> NAME/KEY: MISC_FEATURE
<222> LOCATION: (5)..(6)
<223> OTHER INFORMATION: bAla
<220> FEATURE:
<221> NAME/KEY: MISC_FEATURE
<222> LOCATION: (8)..(9)
<223> OTHER INFORMATION: bAla
<220> FEATURE:
<221> NAME/KEY: MISC_FEATURE
<222> LOCATION: (11)..(12)
<223> OTHER INFORMATION: bAla
<220> FEATURE:
<221> NAME/KEY: MISC_FEATURE
<222> LOCATION: (13)..(13)
<223> OTHER INFORMATION: -Amide

<400> SEQUENCE: 4

Cys Ala Ala Lys Ala Ala Lys Ala Ala Lys Ala Ala Lys
1               5                   10

<210> SEQ ID NO 5
<211> LENGTH: 7
<212> TYPE: PRT
<213> ORGANISM: Artificial
<220> FEATURE:
<223> OTHER INFORMATION: artificial peptidic carrier
<220> FEATURE:
<221> NAME/KEY: MISC_FEATURE
<222> LOCATION: (2)..(3)
<223> OTHER INFORMATION: bAla
<220> FEATURE:
```

```
<221> NAME/KEY: MISC_FEATURE
<222> LOCATION: (5)..(6)
<223> OTHER INFORMATION: bAla
<220> FEATURE:
<221> NAME/KEY: MISC_FEATURE
<222> LOCATION: (7)..(7)
<223> OTHER INFORMATION: optionally, -Amide

<400> SEQUENCE: 5

Cys Ala Ala Lys Ala Ala Lys
1               5

<210> SEQ ID NO 6
<211> LENGTH: 6
<212> TYPE: PRT
<213> ORGANISM: Artificial
<220> FEATURE:
<223> OTHER INFORMATION: artificial peptidic carrier

<400> SEQUENCE: 6

Phe Phe Val Leu Lys Cys
1               5

<210> SEQ ID NO 7
<211> LENGTH: 5
<212> TYPE: PRT
<213> ORGANISM: Artificial
<220> FEATURE:
<223> OTHER INFORMATION: artificial peptide, cell surface receptor
      ligand
<220> FEATURE:
<221> NAME/KEY: MISC_FEATURE
<222> LOCATION: (1)..(1)
<223> OTHER INFORMATION: Formyl-

<400> SEQUENCE: 7

Met Leu Phe Lys Cys
1               5
```

DRUG-POLYMER CONJUGATES COUPLED TO A PEPTIDIC CARRIER

CROSS-REFERENCE TO RELATED APPLICATIONS

This application is a National Stage of International Application No. PCT/US2006/005729, filed Feb. 16, 2006, which claims priority under 35 U.S.C. §119(e) to U.S. Provisional Application Ser. No. 60/653,125, filed Feb. 16, 2005, the disclosure of both of which are incorporated herein by reference.

BACKGROUND OF THE INVENTION

Polymer scaffolds have been employed in order to provide a base structure for macromolecular conjugates. Commercially available poly(ethylene glycol) scaffolds suffer from a variety of problems including the lack of attachment sites and polydispersity. For example, the following two different PEG carrier conjugates had previously been used for linking multiple copies of two different effector substances. In one publication, Zhang et al., "Multiple peptide conjugates for binding β-amyloid plaques of Alzheimer's disease," Bioconjugate Chemistry 14, 86-92 (2003), 6 copies of the D-amino acid peptide, phe-phe-val-leu-lys-cys (SEQ ID NO: 6) and 2 copies of the reporter group, biotin, were linked to an 8-arm branched PEG (Nektar Therapeutics, Ala, USA). In another publication, Pooyan et al., "Conjugates bearing multiple formyl-methionyl peptides display enhanced binding to but not activation of phagocytic cells," Bioconjugate Chemistry 13, 216-223 (2002), varying amounts of the peptide, N-formyl-Met-Leu-Phe (f-MLF), were linked to either an 8-arm branched PEG to form about 4 copies of peptide and 4 copies of the reporter group, digoxigenin, were linked to the 8-arm PEG. In order to arrive at this ratio of effectors, one of them must be attached first and then quantitated. The second effector is then added and either quantitated or assumed to fill the sites not occupied by the first effector. Furthermore, there should be a distribution of appended effectors. That is, there might be 4 copies of peptide and 4 copies of digoxigenin on a large portion of carrier PEGs, but there will also be some carriers having 3 and 5 or 2 and 6 copies due to the randomness of the reaction sites on the carrier. This is an example of polydispersity, since the f-MLF peptide, N-formyl-Met-Leu-Phe and the digoxigenin are present in different ratios on individual carrier molecules.

There exists a need for a means by which monodispersed conjugates of two substances or a polymer scaffold can be prepared in high yields to eliminate the need to isolate a desired conjugate fraction.

SUMMARY OF THE INVENTION

This need is met by the present invention.

There is provided, in accordance with the present invention, a monodisperse macromolecular conjugate composition for in-vivo delivery of a therapeutic agent having a peptidic carrier conjugated with: (a) one or more effectors and (b) one or more therapeutic agents, wherein the peptidic carrier includes at least two different orthogonal pendant reactive groups each for specific attachment of a predetermined effector or therapeutic agent and at least one effector or therapeutic agent is attached to at least one of the pendant reactive group on the peptidic carrier via a water-soluble polymer.

In one embodiment, the peptidic carrier is selected from a peptide, a peptide mimetic, a pseudopeptide, and a peptide-related compound. The peptidic carrier can have any number of amino acid subunits, amino acid-like subunits, or a combination thereof. In one embodiment, the peptidic carrier includes 1 to 50 amino acid subunits, amino acid-like subunits, or a combination thereof, preferably 2 to 20 amino acid subunits, amino acid-like subunits, or a combination thereof, and more preferably 4 to 16 amino acid subunits, amino acid-like subunits, or a combination thereof. In a preferred embodiment, the peptidic carrier includes cysteine, lysine, or a combination thereof.

In one embodiment, the peptidic carrier is stabilized against proteolysis. Stabilization is accomplished, for example, by using D-amino acids or by capping the N-terminus moieties such as with an acetyl group or by capping the C-terminus with an amide group. Similarly the N- and C-terminus can be blocked using different moieties. Also, certain amino acids such as beta-alanine, which is stable against proteolysis, is preferably incorporated into the peptidic carrier. This addition would also help to overcome stearic hindrance in synthesis, providing high yields.

Each reactive group may be independently selected from a thiol, a primary amine, a carboxylic acid, an alcohol, a phenol, a hydrazide, a hydrazone, a ketone, an oxime, and an aldehyde. In a specific embodiment, the peptidic carrier includes one or more pendant groups formed thereon independently selected from a thiol, a primary amine, a carboxylic acid, an alcohol, and a phenol and the effector or therapeutic agent is conjugated thereto by means of a group reactive therewith on the effector or therapeutic agent. In an additional embodiment, the peptidic carrier includes one or more pendant groups formed thereon independently selected from a thiol, a primary amine, a carboxylic acid, an alcohol, and a phenol and the effector or therapeutic agent is conjugated thereto by means of a water-soluble polymer on the effector or therapeutic agent.

In one embodiment, the peptidic carrier includes at least one first reactive group selected from thiols, primary amines, carboxylic acids, alcohols, phenols, hydrazides, hydrazones, ketones, oximes, and aldehydes, to which a first therapeutic agent or first effector is conjugated; and at least one second reactive group orthogonal to said at least one first reactive group and selected from thiols, primary amines, carboxylic acids, alcohols, phenols, hydrazides, hydrazones, ketones, oximes, and aldehydes to which a second therapeutic agent or second effector is conjugated.

In another embodiment, the first therapeutic agent is an anti-retroviral therapeutic agent, preferably an AIDS chemotherapeutic agent.

In one embodiment, the first effector is a cell surface receptor ligand, preferably FMLF, mannose, or folate.

In another embodiment, the second therapeutic agent is an antineoplastic therapeutic agent, preferably campothecin, paclitaxel, or doxorubicin.

In one embodiment, the second effector is a cell penetrating peptide, preferably R.I.Tat9-KC.

In one embodiment, at least one orthogonal pendant reactive group on the peptidic carrier is chemoselective with a reactive group attached to the water soluble polymer prior to conjugation. In another embodiment, at least one orthogonal pendant reactive group on the peptidic carrier is chemoselective with a reactive group attached to the effector prior to conjugation. In yet another embodiment, one of two orthogonal pendant reactive groups on the peptidic carrier is chemoselective with a reactive group attached to the water soluble polymer prior to conjugation and the other orthogonal pendant reactive group on the peptidic carrier is chemoselective with a reactive group attached to the effector prior to conjugation. Thus, the following configurations are possible:
- peptidic carrier—effector
- peptidic carrier—therapeutic agent
- peptidic carrier—water soluble polymer—effector
- peptidic carrier—water soluble polymer—therapeutic agent
- peptidic carrier—water soluble polymer The composition can have any number of different orthogonal reactive groups or any number of copies of each group. In a preferred embodiment, there are 2 to 5 different orthogonal reactive groups attached to the peptidic carrier. In another embodiment, there are 1 to 20 copies of each type of reactive group, preferably 2 to 6 copies of each reactive group.

In a preferred embodiment, the water-soluble polymer is poly(ethylene glycol), which is linear or branched. The poly(ethylene glycol) can have any molecular weight. In a preferred embodiment, the poly(ethylene glycol) has a molecular weight of from 1,000 to 100,000 g/mol, more preferably from 2,000 to 5,000 g/mol.

The composition can have any number of different effectors conjugated with the peptidic carrier. In a preferred embodiment, there are up to 10 different effectors. In another embodiment, there are 1 to 50 copies of each type of effector, preferably 1 to 4 copies of each type of effector conjugated with the peptidic carrier. In a specific embodiment, the effector is selected from ligands or substrates for receptors, membrane influx or efflux transporters, and enzymes; tissue- and cell-specific targeting groups; permeability enhancers, and modifiers of cell-machinery, cell-signaling or cell-disposition.

Further, the composition can have any number of different therapeutic agents conjugated with the peptidic carrier. In a preferred embodiment, there are up to 10 different therapeutic agents. In another embodiment, there are 1 to 50 copies of each type of therapeutic agent, preferably 1 to 4 copies of each type of therapeutic agent conjugated with the peptidic carrier.

Also provided is a method for preparing a monodisperse macromolecular conjugate composition for in-vivo delivery of a therapeutic agent, wherein the macromolecular conjugate includes a peptidic carrier conjugated with one or more effectors and one or more therapeutic agents, wherein the method includes the steps of (a) providing a peptidic carrier having at least two different orthogonal pendant reactive groups each for specific attachment of a predetermined effector or therapeutic agent, in which the peptidic carrier is selected from a peptide, a peptide mimetic, a pseudopeptide, and a peptide-related compound; (b) attaching an effector to the peptidic carrier by means of a water-soluble polymer such that each copy of an effector is attached to the same reactive groups on each peptidic carrier in the composition; and (c) attaching a therapeutic agent to the peptidic carrier by means of a water-soluble polymer such that each copy of a therapeutic agent is attached to the same reactive groups on each peptidic carrier in the composition.

Also provided is a monodisperse macromolecular conjugate composition including a peptidic carrier, wherein the peptidic carrier includes at least two different orthogonal pendant reactive groups, wherein at least one of the pendant reactive groups on the peptidic carrier is attached to a water-soluble polymer.

In one embodiment, the peptidic carrier includes an amino acid sequence selected from Cys-beta Ala-Lys; (SEQ ID NO: 1); Cys-(beta Ala-Lys)$_6$(SEQ ID NO: 2); Acetyl-Cys-(beta Ala-beta Ala-Lys)$_2$-Amide(SEQ ID NO: 3); Acetyl-Cys-(beta Ala-beta Ala-Lys)$_4$-Amide(SEQ ID NO: 5); and Cys-(beta Ala-beta Ala-Lys)$_2$(SEQ ID NO: 5).

Also provided are methods for treating conditions linked to viral disorders, microbial disorders, hyperproliferative disorders, drug addiction, or mental health disorders, the method includes administering to a patient in need thereof an effective amount of a monodisperse macromolecular conjugate composition.

The configurations described herein provide the desired monodispersity. However, there can be an intrinsic polydispersity (a natural characteristic of large polymers) in the water soluble polymer which is unrelated to the monodispersity described above in this paragraph.

DETAILED DESCRIPTION OF THE INVENTION

Figure 1:
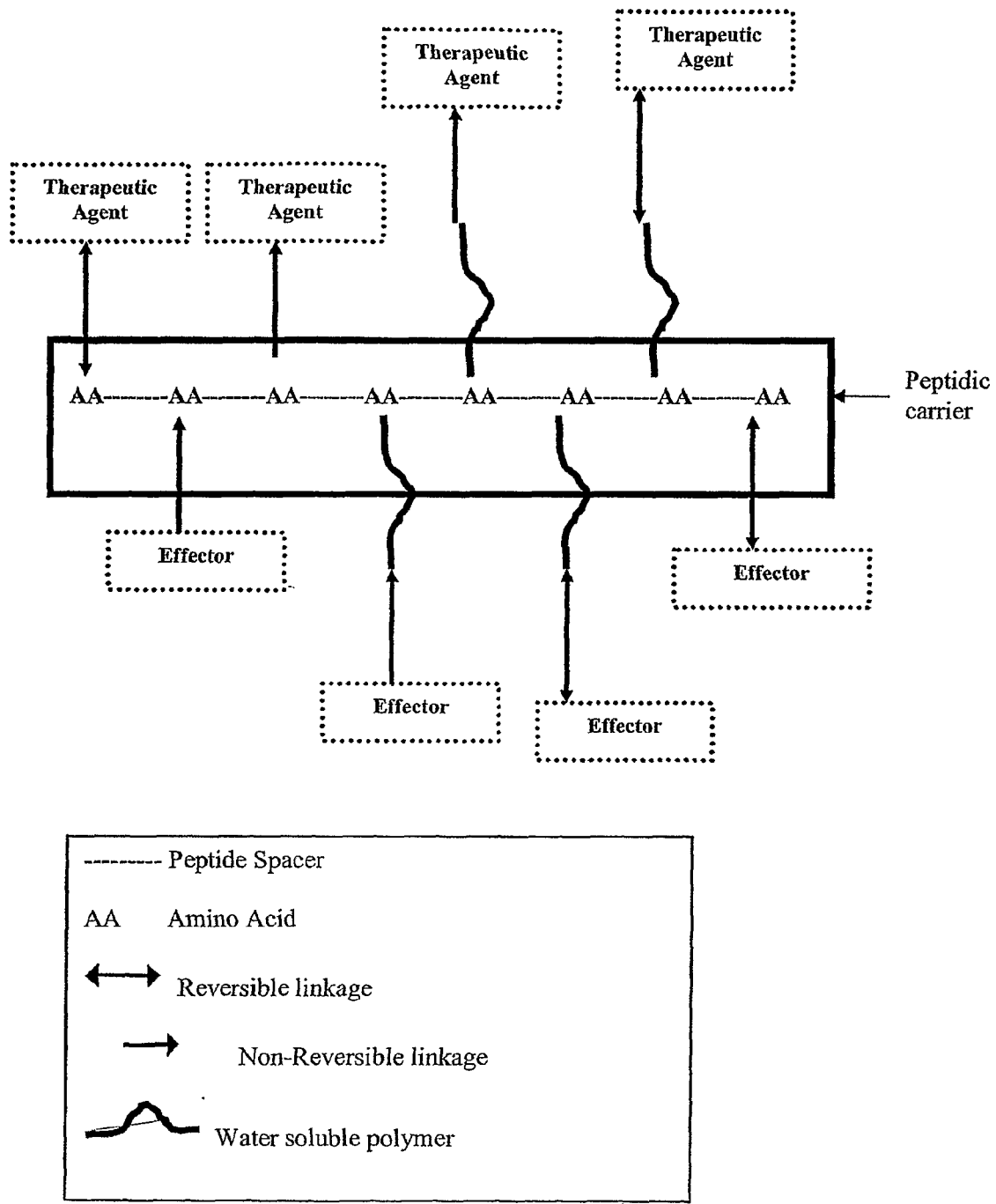
FIG. 1: Depicts a schematic representation of a macromolecular conjugate of the present invention.

The present invention provides a monodisperse macromolecular conjugate composition comprising a peptidic carrier conjugated with one or more effectors and one or more therapeutic agents, wherein at least one effector or therapeutic agent is attached to a pendant reactive group on the peptidic carrier directly or via a water-soluble polymer. The use of orthogonal and separate conjugation reactions, in which an excess of effector or therapeutic agent drives each reaction to completion, provides a monodisperse composition having essentially the same number of effectors and therapeutic agents conjugated to each peptidic carrier. Any polydispersity in the water soluble polymer is irrelevant and unrelated to the monodispersity of the macromolecule conjugate.

As used herein, the following terms have the following meanings:

A "pseudodipeptide" is a modified dipeptide structural unit that contains a surrogate bond(s) or amino acid residue(s).

By "peptidomimetic" is meant a peptide analog containing one or more unnatural amino acids (e.g. unnatural side chains, unnatural chiralities, N-substituted amino acids, or beta amino acids), unnatural topologies (e.g. cyclic or branched) or unnatural chemical derivatives (e.g. methylated or terminally blocked), or any molecule, other than a peptide containing natural amino acids, that is synthesized by a ribosome, including those products that have unnatural backbones and even those with partially or totally substituted amide (peptide) bonds with ester, thioester or other linkages.

"Amino acid-like" refers to amino acid analogs.

"Peptide-related" refers to peptide analogs.

"Effector" is a substance used in combination with a therapeutic agent to aid the action of the therapeutic agent. The term effector is broadly used in this patent to include a variety of molecules such as ligands or substrates for receptors, membrane influx or efflux transporters, and enzymes; tissue- and cell-specific targeting groups; permeability enhancers, and modifiers of cell-machinery, cell-signaling or cell-disposition. The effector is preferably attached directly to the peptidic carrier or via a water-soluble polymer or in other similar configurations by means of releasable or nonreleasable bonds.

"Therapeutic agent" is a compound that is used for the treatment or prevention of a disease or for improving the well being of a mammal. Examples of therapeutic agents include but are not limited to systemic anti-infective agents, antimalarials, anti-neoplastic therapeutic agents and small-interfering RNAs (siRNAs).

Examples of systemic anti-infective agents include AIDS chemotherapeutic agents such as NUCLEOSIDE REVERSE TRANSCRIPTASE INHIBITORS, such as, Abacavir, Didanosine, Emtricitabine, Lamivudine, Stavudine, Tenefovir, Zalcitabine, and Zidovudine; NON NUCLEOSIDE REVERSE TRANSCRIPTASE INHIBITORS, such as, Delavirdine, Efavirenz, and Nevirapine; PROTEASE INHIBITORS, such as, Amprenavir, Atazanavir, Fosamprenavir, Indinavir, Lopinavir, Nelfinavir, Ritonavir, Saquinavir, and Tipranavir; ENTRY /FUSION INHIBITORS, such as Enfuvirtide; and TAT INHIBITORS, such as, R.I. CK Tat9.

Examples of antineoplastic agents include Abarelix, Aldesleukin, Alemtuzumab, Alitretinoin, Allopurinol, Altretamine, Amifostine, Anastrozole, arsenic trioxide, asparaginase, azacitidine, bevacuzimab, bleomycin, bortezomib, capecitabine, carboplatin, carmustine, celecoxib, cetuximab, chlorambucil, cisplatin, cladribine, clofarabine, cyclophosphamide, cytarabine, dacarbazine, daunorubicin, daunomycin, dexrazoxane, docetaxel, doxorubicin, epirubicin, Epoetin alfa, Erlotinib, Estramustine, etoposide phosphate, etoposide, VP-16, exemestane, Filgrastim, Floxuridine, Fludarabine, fluorouracil, 5-FU, fulvestrant, gefitinib, gemcitabine, gemtuzumab, goserelin acetate, histrelin acetate, hydroxyurea, idarubicin, ifosfamide, imatinib mesylate, interferon alfa 2a, irinotecan, lenalidomide, letrozole, leucovorin, Leuprolide Acetate, Levamisole, lomustine, CCNU, meclorethamine, nitrogen mustard, megestrol acetate, melphalan, L-PAM, mercaptopurine, 6-MP, mesna, methotrexate, methoxsalen, mitomycin C, mitotane, mitoxantrone, nelarabine, Nofetumomab, Oprelvekin, Oxaliplatin, Paclitaxel, Palifermin, Pamidronate, Pegademase, pemetrexed disodium, pentostatin, pipobroman, plicamycin, mithramycin, porfimer sodium, procarbazine, quinacrine, Rasburicase, Rituximab, Sargramostim, Sorafenib, Streptozocin, sunitinib maleate, tamoxifen, temozolomide, teniposide, VM-26, testolactone, thioguanine, 6-TG, thiotepa, topotecan, toremifene, Tositumomab, Trastuzumab, Uracil Mustard, Valrubicin, Vinblastine, Vincristine, Vinorelbine, Zoledronate, and zoledronic acid.

The central peptidic carrier can be used in the preparation of a monodisperse macromolecular conjugate composition by conjugating the pendant functional groups either directly with reactive functional groups on an effector, therapeutic agent, or water-soluble polymer, or by first further functionalizing the pendant functional group to improve its reactivity with or selectivity for a functional group on an effector, therapeutic agent, or water-soluble polymer.

The peptidic carrier can be selected from a peptide, a peptide mimetic, a pseudopeptide, and a peptide-related compound. The peptidic carrier preferably comprises cysteine, lysine, or a combination thereof, and can comprise any number of amino acid subunits, amino acid-like subunits, or a combination thereof. In a preferred embodiment, the peptidic carrier comprises 1 to 50 amino acid subunits, amino acid-like subunits, or a combination thereof. More preferably, the peptidic carrier comprises 2 to 20 amino acid subunits, amino acid-like subunits, or a combination thereof. Most preferred is a peptidic carrier that comprises 4 to 16 amino acid subunits, amino acid-like subunits, or a combination thereof. The peptidic carrier may be stabilized against proteolysis.

Orthogonal pendant reactive groups are used to conjugate the effector, therapeutic agent, and water-soluble polymer to the peptidic carrier. For example, a reactive group on the peptidic carrier may be chemoselective with a reactive group attached to an effector or therapeutic agent prior to conjugation.

If a water-soluble polymer is used to conjugate an effector or therapeutic agent to a pendant group on the peptidic carrier, the pendant reactive group may be chemoselective with a reactive group attached to the water-soluble polymer prior to conjugation. The conjugation of enzymes and other polypeptides with water-soluble polymers is well-known and described in detail in U.S. Pat. No. 4,179,337 to Davis et al., and in Zalipsky, "Functionalized Poly(ethylene glycol) for Preparation of Biologically Relevant Conjugates," Bioconjugate Chem., 6, 150-165 (1995), both of which are incorporated by reference in their entirety herein. The properties of the poly(alkylene oxide) dominate the conjugate.

Suitable water-soluble polymers for use in the present invention include poly(alkylene oxides), such as poly(ethylene glycol) (abbreviated: PEG), poloxamines, and poloxamers; polysaccharides; poly(vinyl alcohols); polypyrrolidone; poly(acrylic acid) and its many water-soluble derivatives such as poly(hydroxyethyl-methacrylate); polyoxyethylated polyols; and the like.

When poly(alkylene oxides) are used, they may be straight chained or branched. Branched poly(alkylene oxides), such as branched PEG, because of their larger spatial volume, are believed to be less likely to penetrate protein crevasses, which are often the binding motifs and active sites of enzymes. Typical poly(alkylene oxides) consist of C2-C4 alkylene oxide groups, separately as homopolymers or in combination. This includes PEGs, poloxamers and poloxamines. The poly(alkylene oxides) can be substituted at one end with an alkyl group, or it may be unsubstituted. The alkyl group, when present, can be a C1-C4 alkyl group, and is typically a methyl group.

The poly(alkylene oxides), when used, typically have weight-average molecular weights between 1,000 to 100,000 g/mol, preferably from 2,000 to 5,000 g/mol. In certain cases, the poly(alkylene oxide) may have as few as 3 or 4 subunits of the formulae, $-(CH_2-CH_2-O-)_3$ or $-(CH_2-CH_2-O-)_4$.

Suitable reactions for coupling an effector or therapeutic agent to a water-soluble polymer are also well known and essentially conventional. A typical reaction involves preparing an activated polymer and thereafter reacting the therapeutic agent or effector with the activated polymer. The reaction using N-hydroxysuccinimide activated mPEG (mPEG-NHS) described by Davis et al. can be used. mPEG-NHS is commercially available from Shearwater Polymers, Inc. of Huntsville, AL, now known as Nektar Therapeutics.

The conjugation of a pharmaceutically active compound, such as an effector or therapeutic agent, to the pendant functional group of an amino acid or peptide sequence is essentially conventional and described in detail, for example, in U.S. Pat. No. 5,455,027 to Zalipsky et al., as well as in Nathan et al., Bioconjugate Chemistry 4, 54-62 (1993) and Nathan et al., Macromolecules, 25, 4476-84 (1992). The disclosures of all three publications are incorporated herein by reference.

A typical conjugate of the present invention is depicted in FIG. 1. Various types of linkages are shown. Therapeutic agents and effectors are directly conjugated to the peptidic carrier via water soluble polymers. Means by which effectors, therapeutic agents, or water-soluble polymers may be conjugated to the peptidic carrier include the following Examples:

| Peptidic carrier + | Polymer --> | product |
|---|---|---|
| R—NH$_2$ + (amine) | Polymer-COOH --> (carboxylic acid) | R—NH—CO-Polymer (amide) |
| R—NH$_2$ + (amine) | Polymer-CHO --> (aldehyde) | R—N=CH-Polymer (Schiff base) |
| R—NH—NH$_2$ + (hydrazide) | Polymer-CHO --> (aldehyde) | R—NH—N=CH-Polymer (Hydrazide Schiff Base) |
| R—O—NH$_2$ + (oxime) | Polymer-CHO --> (aldehyde) | R—O—N=CH-Polymer (Oxime Schiff Base) |
| R—SH + (thiol) | Polymer-S-thiopyridine --> (thiopyridine disulfide) | R—S—S-Polymer (disulfide) |
| R—SH + (thiol) | Polymer-maleimide --> (maleimide) | R—S-Polymer (thioether) |
| R—SH + (thiol) | Polymer-vinylsulfone --> (vinylsulfone) | R—S-Polymer (vinylsulfone) |

R=other chemical group. Opposite pairs can be obtained by switching the reactive groups on R on the peptide carrier to the polymer. For example, to obtain the amide product,

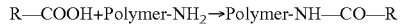

R—COOH+Polymer-NH$_2$→Polymer-NH—CO—R

Some suitable reactive groups for use in the present invention include thiols, primary amines, carboxylic acids, alcohols, phenols, hydrazides, hydrazones, ketones, oximes, and aldehydes. Any of these reactive groups can be present or formed on the effector, therapeutic agent, water-soluble polymer, or peptidic carrier.

For example, pendant ketones and aldehydes may be formed by the oxidation of first or second degree hydroxyl groups on amino acid or amino acid-like subunits. Ketones and aldehydes can be further reacted with hydrazine to form a hydrazone or with hydroxylamine to form an oxime. Acyl hydrazides can be formed by reacting a carboxyl group on an amino acid or amino acid-like subunit with an alkyl carbazate, which can then be converted to an acyl hydrazide by reaction with a strong acid. Alternatively, esters can be used to form acyl hydrazides by reaction with hydrazines.

The peptidic carrier can contain any number of different pendant reactive groups. In a preferred embodiment, 2 to 5 different orthogonal reactive groups are attached to the central peptidic carrier. Further, the peptidic carrier can contain any number of copies of each pendant reactive group. Preferably, there are 1 to 20 copies of each reactive group attached to the peptidic carrier. More preferably, there are 2 to 6 copies of each reactive group.

Figure 2:
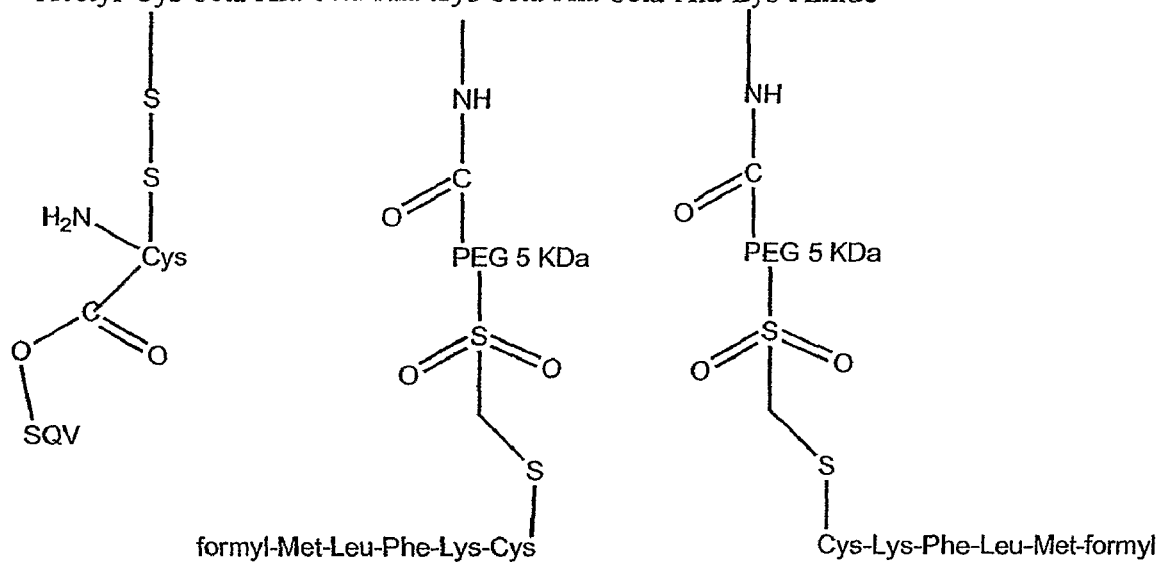
FIG. 2: Illustrates the chemical structure of an example of a macromolecule conjugate with a therapeutic agent (e.g., saquinavir, (SQV)) and 2 copies of effectors (f-MLF).

A specific conjugate is depicted in FIG. 2, which depicts a macromolecule conjugate with a therapeutic agent (e.g., saquinavir, (SQV)) and 2 copies of effectors (f-MLF). The drug is attached via a reversible linkage to the peptidic carrier. The ester and disulfide linkage can be broken to release the drug. The modified f-MLF moieties are attached irreversibly via PEG to the peptidic carrier.

Another aspect of the invention involves a pharmaceutical composition as described above, wherein the macromolecular conjugate is used in a pharmaceutically acceptable excipient. The term "pharmaceutically acceptable excipient" refers to those components in the particular dosage form employed which are inert and are typically employed in the pharmaceutical arts to formulate a particular active compound. This may include, without limitation, liquids used to formulate the particular pharmaceutical product. Examples of excipients include diluents, solubilizers, suspending agents, penetration enhancers, solvents, emollients, thickeners, dispersants, transdermal delivery components, buffers, stabilizers, preservatives and the like. Each of these terns is understood by those of ordinary skill.

Numerous methods are presently available for administering the composition of the present invention to a mammal. The composition may be introduced to the mammal parenterally, transdermally, intraocularly, and by inhalation. Preferably, administration is parenteral, e.g., via intravenous injection, and also includes, but is not limited to, intra-arterially, intramuscular, intradermal, subcutaneous, intraperitoneal, intraventricular, and intracranial administration.

A method for preparing a monodisperse macromolecular conjugate composition for in-vivo delivery of a therapeutic agent is also provided, wherein the macromolecular conjugate comprises a peptidic carrier conjugated with one or more effectors and one or more therapeutic agents, wherein the method comprises the steps of (a) providing a peptidic carrier comprising at least two different orthogonal pendant reactive groups each for specific attachment of a predetermined effector or therapeutic agent, in which the peptidic carrier is selected from a peptide, a peptide mimetic, a pseudopeptide, and a peptide-related compound; (b) attaching an effector to the peptidic carrier by means of a water-soluble polymer such that each copy of an effector is attached to the same reactive group on each peptidic carrier in the composition; and (c) attaching a therapeutic agent to the peptidic carrier by means of a water-soluble polymer such that each copy of a therapeutic agent is attached to the same reactive groups on each peptidic carrier in the composition.

During the preparation of the macromolecular conjugates of the present invention, the water-soluble polymer, the effector, and the therapeutic agent can be conjugated to the peptidic carrier in any order. Accordingly, the peptidic carrier can be conjugated with effectors, therapeutic agents, and water-soluble polymers by any combination of the modes of conjugation set forth above.

The conjugation reactions utilize an organic solvent in which the reactants are soluble or in buffered water. Examples of suitable organic solvents include dimethyl formamide (DMF), acetonitrile (ACN), dioxane, dichloromethane (DCM). The appropriate quantities of peptidic carrier and effector or therapeutic agent are dissolved in the solvent. The solvent may be heated slightly to dissolve the reactants. An excess of the effector or the therapeutic agent is preferred to ensure substantial conjugation of the pendant functional groups of the peptidic carrier. The total solution concentration (w/v%) of both compounds combined is not critical, and will vary depending upon the solubility of the materials. Complete solubility of the effector or therapeutic agent is not critical because the effector or therapeutic agent will be solubilized upon conjugation with the peptidic carrier. Activating reagents, coupling agents, or catalysts may also be added.

The reaction mixture is typically stirred between about 0 and about 30° C. until completion of the reaction, typically within 24 hours and usually overnight. Temperatures close to or below room temperature are preferred to preserve the integrity of the effector or therapeutic agent.

Any insolubles that form may be removed by filtration. The conjugate is then precipitated more than once with a solvent in which it has poor solubility, e.g. ether, filtered and purified further by dialysis; column chromatography: reverse-phase, silica gel, ion-exchange and size exclusion (gel permeation); low pressure or high performance liquid chromatography (HPLC). The product is then dried in vacuo.

Compounds of the present invention can be prepared according to the following exemplary schemes, wherein the composition and size of the peptide carrier and PEG can vary from those depicted in the general procedures that follow. One skilled in the art would be able to accomplish such variations.

Acetyl-Cys(TP)-beta Ala-beta Ala-Lys-beta Ala-beta Ala-Lys-Amide

| NHS-PEG5000-VS
| Phosphate Buffer pH = 7.5
| 6 h stirring/RT
↓

Acetyl-Cys(TP)-beta Ala-beta Ala-Lys-beta Ala-beta Ala-Lys-Amide
　　　　　　　　　　　|　　　　　　　　　　　　　|
　　　　　　　　　VS-PEG5000　　　　　　　PEG5000-VS

| f-MLFKC
| Phosphate Buffer pH = 8.0
| 6 h stirring/RT
↓

Acetyl-Cys-beta Ala-beta Ala-Lys-beta Ala-beta Ala-Lys-Amide
　　　|　　　　　　　　　　|　　　　　　　　　　　　　　|
　　　S　　　f-MLFKC-PEG5000　　　　　　　PEG5000-CKFLM-f
　　　|
　　　S
　　　|
　f-MLFKC

| DTT
| Phosphate Buffer pH = 8.0
| 6 h stirring/RT
↓

Acetyl-Cys-beta Ala-beta Ala-Lys-beta Ala-beta Ala-Lys-Amide
　　　　　　　　　　|　　　　　　　　　　　　|
　　　　f-MLFKC-PEG5000　　　　　　PEG5000-CKFLM-f i. TP-TP
　 Phosphate Buffer pH = 8.0
　 6 h stirring/RT
ii. SQV-Cys-ester
　 Phosphate Buffer pH = 8.0
　 6 h stirring/RT
↓

Acetyl-Cys-beta Ala-beta Ala-Lys-beta Ala-beta Ala-Lys-Amide
　　　|　　　　　　　　|　　　　　　　　　　　　|
　　　S　　　f-MLFKC-PEG5000　　　　　PEG5000-CKFLM-f
　　　|
　　　S
　　　|
　　SQV Scheme II:

Acetyl-Cys(TP)-(beta Ala-beta Ala-Lys-beta Ala-beta Ala-Lys)$_2$-Amide

| NHS-PEG5000-VS
| Phosphate Buffer pH = 7.5
| 6 h stirring/RT
↓

-continued

Acetyl-Cys(TP)-(beta Ala-beta Ala-Lys-beta Ala-beta Ala-Lys)$_2$-Amide
　　　　　　　　　|　　　　　　　　　　　　　|
　　　　　　VS-PEG5000　　　　　　　PEG5000-VS

| f-MLFKC
| Phosphate Buffer pH = 8.0
| 6 h stirring/RT
↓

Acetyl-Cys-(beta Ala-beta Ala-Lys-beta Ala-beta Ala-Lys)$_2$-Amide
　　　|　　　　　　　　|　　　　　　　　　　　　|
　　　S　　　f-MLFKC-PEG5000　　　　　PEG5000-CKFLM-f
　　　|
　　　S
　　　|
　f-MLFKC

| DTT
| Phosphate Buffer pH = 8.0
| 6 h stirring/RT
↓

Acetyl-Cys-(beta Ala-beta Ala-Lys-beta Ala-beta Ala-Lys)$_2$-Amide
　　　　　　　　　|　　　　　　　　　　　|
　　　　f-MLFKC-PEG5000　　　　　PEG5000-CKFLM-f i. TP-TP
　 Phosphate Buffer pH = 8.0
　 6 h stirring/RT
ii. SQV-Cys-ester
　 Phosphate Buffer pH = 8.0
　 6 h stirring/RT
↓

Acetyl-Cys-(beta Ala-beta Ala-Lys-beta Ala-beta Ala-Lys)$_2$-Amide
　　　|　　　　　　　　|　　　　　　　　　　|
　　　S　　　f-MLFKC-PEG5000　　　　PEG5000-CKFLM-f
　　　|
　　　S
　　　|
　　SQV Scheme III:

Acetyl-Cys(TP)-beta Ala-beta Ala-Lys-beta Ala-beta Ala-Lys-Amide

| NHS-PEG5000-VS
| Phosphate Buffer pH = 7.5
| 6 h stirring/RT
↓

Acetyl-Cys(TP)-beta Ala-beta Ala-Lys-beta Ala-beta Ala-Lys-Amide
　　　　　　　　　|　　　　　　　　　　　|
　　　　　　VS-PEG5000　　　　　　PEG5000-VS

| f-MLFKC
| Phosphate Buffer pH = 8.0
| 6 h stirring/RT
↓

-continued

Acetyl-Cys-beta Ala-beta Ala-Lys-beta Ala-beta Ala-Lys-Amide
|
S    f-MLFKC-PEG5000    PEG5000-CKFLM-f
|
S
|
f-MLFKC

| DTT
| Phosphate Buffer pH = 8.0
| 6 h stirring/RT
↓

Acetyl-Cys-beta Ala-beta Ala-Lys-beta Ala-beta Ala-Lys-Amide
|
f-MLFKC-PEG5000    PEG5000-CKFLM-f

| i. HBVS
|    Phosphate Buffer pH = 8.0
|    6 h stirring/RT
| ii. R.I. Tat-KC
|    Phosphate Buffer pH = 8.0
|    6 h stirring/RT
↓

Acetyl-Cys-beta Ala-beta Ala-Lys-beta Ala-beta Ala-Lys-Amide
|
R.I. Tat-KC  f-MLFKC-PEG5000    PEG5000-CKFLM-f Scheme IV:

Fmoc—NH-Cys-beta Ala-Lys-NH2

| Boc-PEG3400-NHS
| 1% DIEA/DMF
| 12 h stirring at RT
↓

Fmoc—NH-Cys-beta Ala-Lys-NH—C(=O)—PEG3400-Boc

| i. 20% Piperidine/DMF
|    30 mins stirring at RT
| ii. ³H Aetic Anhydride/MeOH
|    12 h stirring at RT
↓

*CH₃—C(=O)—NH-Cys-beta Ala-Lys-NH—C(=O)—PEG3400-Boc

Scheme V:

Fmoc—NH-Cys-(beta Ala-Lys-NH₂)₆

| Boc-PEG3400-NHS
| 1% DIEA/DMF
| 12 h stirring at RT
↓

Fmoc—NH-Cys-(beta Ala-Lys-NH—C(=O)—PEG3400-Boc)₆

| i. 20% Piperidine/DMF
|    30 mins stirring at RT
| ii. ³H Aetic Anhydride/MeOH
|    12 h stirring at RT
↓

*CH₃—C(=O)—NH-Cys-(beta Ala-Lys-NH—C(=O)—PEG3400-Boc)₆

Scheme VI:

Acetyl-Cys(SH)-beta Ala-beta Ala-Lys-beta Ala-beta Ala-Lys-Amide

| mPEG5000-OPSS
| Phosphate Buffer pH = 7.5
| 6 h stirring/RT
↓

Acetyl-Cys-beta Ala-beta Ala-Lys-beta Ala-beta Ala-Lys-Amide
|
S
|
S
|
mPEG5000

| i. GMBS
|    Phosphate Buffer pH = 7.5
|    2 h stirring/RT
| ii. R.I. Tat-KC
|    Phosphate Buffer pH = 7.0
|    18 h stirring/RT
↓

Acetyl-Cys-beta Ala-beta Ala-Lys-beta Ala-beta Ala-Lys-Amide
|                          R.I. Tat-KC    R.I. Tat-KC
S
|
S
|
mPEG5000

Scheme VII:

Acetyl-Cys(SH)-beta Ala-beta Ala-Lys-beta Ala-beta Ala-Lys-Amide

| PEG5000-(Mal)₂
| Phosphate Buffer pH = 7.5
| 16 h stirring/RT
↓

Acetyl-Cys-beta Ala-beta Ala-Lys-beta Ala-beta Ala-Lys-Amide
|
PEG5000
|
Acetyl-Cys-beta Ala-beta Ala-Lys-beta Ala-beta Ala-Lys-Amide

| i. VS-PEG5000-NHS
|   Phosphate Buffer pH = 7.5
|   6 h stirring/RT
| ii. R.I. Tat-KC
|   Phosphate Buffer pH = 7.0
|   18 h stirring/RT
↓

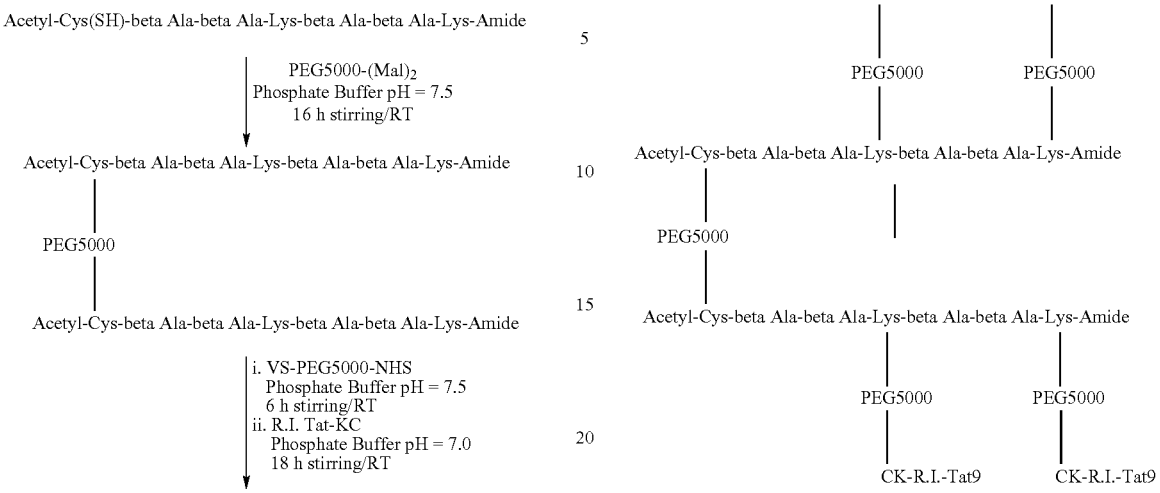

-continued

CK-R.I.-Tat9        CK-R.I.-Tat9
|                   |
PEG5000             PEG5000
|                   |
Acetyl-Cys-beta Ala-beta Ala-Lys-beta Ala-beta Ala-Lys-Amide
|
PEG5000
|
Acetyl-Cys-beta Ala-beta Ala-Lys-beta Ala-beta Ala-Lys-Amide
|                   |
PEG5000             PEG5000
|                   |
CK-R.I.-Tat9        CK-R.I.-Tat9

Scheme VIII:

Acetyl-Cys(SH)-beta Ala-beta Ala-Lys-beta Ala-beta Ala-Lys-Amide

| PEG3400-(OPSS)₂
| Phosphate Buffer pH = 7.5
| 16 h stirring/RT
↓

Acetyl-Cys-beta Ala-beta Ala-Lys-beta Ala-beta Ala-Lys-Amide
|
S
|
S
|
PEG5000
|
S
|
S
|
Acetyl-Cys-beta Ala-beta Ala-Lys-beta Ala-beta Ala-Lys-Amide

| i. VS-PEG5000-NHS
|   Phosphate Buffer pH = 7.5
|   6 h stirring/RT
| ii. R.I. Tat-KC
|   Phosphate Buffer pH = 7.0
|   18 h stirring/RT
↓

-continued
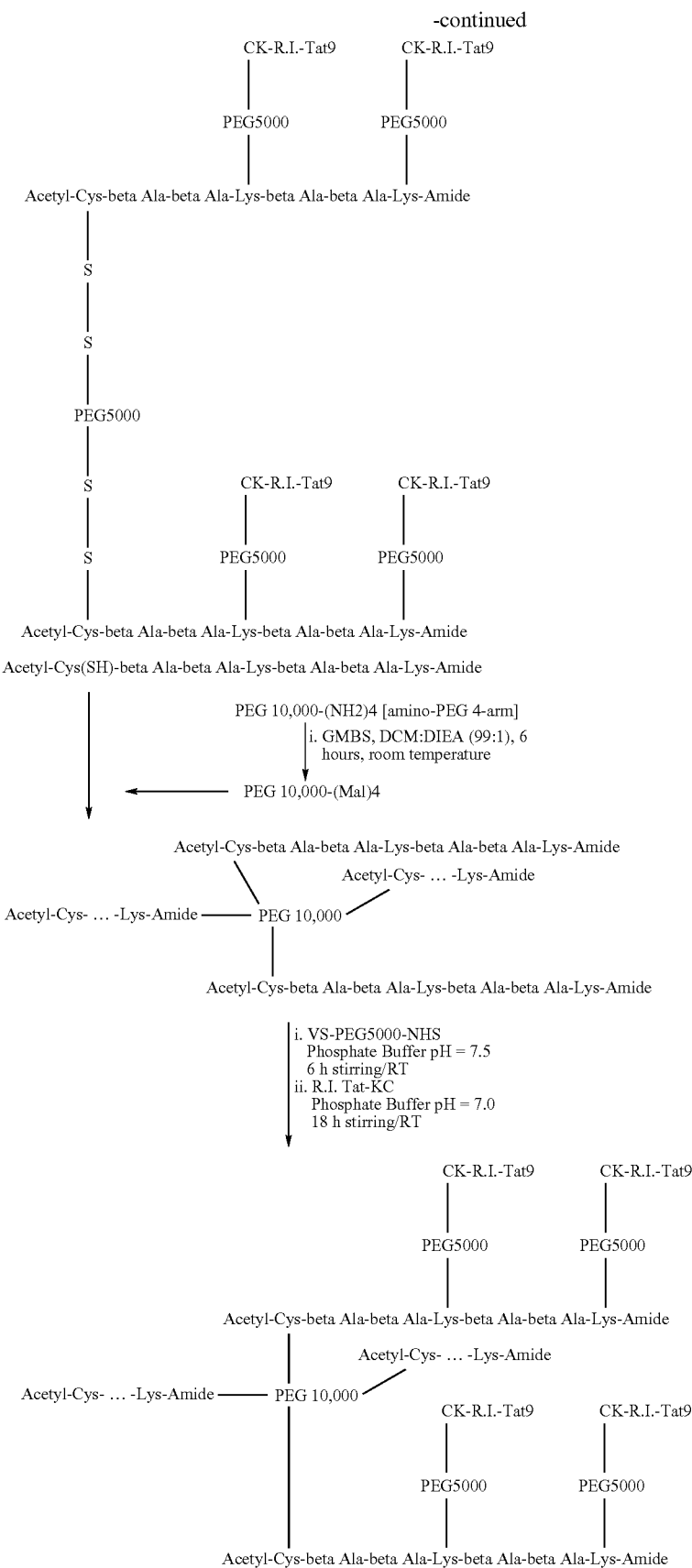

-continued

Acetyl-Cys(SH)-beta Ala-beta Ala-Lys-beta Ala-beta Ala-Lys-Amide

PEG 10,000-(NH2)4 [amino-PEG 4-arm]
i. SPDP, PBS (pH = 7.0): DMSO (75:25), pH = 7.0, 6 hours, room temperature

← PEG 10,000-(TP)4

Acetyl-Cys-beta Ala-beta Ala-Lys-beta Ala-beta Ala-Lys-Amide
|
S
|
S
|
Acetyl-Cyl- ... -Lys-Amide ——— S ——— S ——— PEG 10,000
|                                              \S
S                                               \
|                                                S
S                                                 \
|                                                  Acetyl-Cys-beta Ala-beta Ala-Lys-beta Ala-beta Ala-Lys-Amide
Acetyl-Cys-beta Ala-beta Ala-Lys-beta Ala-beta Ala-Lys-Amide i. VS-PEG5000-NHS
   Phosphate Buffer pH = 7.5
   6 h stirring/RT
ii. R.I. Tat-KC
    Phosphate Buffer pH = 7.0
    18 h stirring/RT CK-R.I.-Tat9   CK-R.I.-Tat9
|              |
PEG5000        PEG5000
 \             /
  Acetyl-Cys-beta Ala-beta Ala-Lys-beta Ala-beta Ala-Lys-Amide
  |
  S
  |
  S
  |
Acetyl-Cyl- ... -Lys-Amide ——— S ——— S ——— PEG 10,000        CK-R.I.-Tat9   CK-R.I.-Tat9
                                             \S              |              |
                                              \              PEG5000        PEG5000
                                               S              \             /
                                                \              Acetyl-Cys-beta Ala-beta Ala-Lys-beta Ala-beta Ala-Lys-Amide
                                                 S
Acetyl-Cys-beta Ala-beta Ala-Lys-beta Ala-beta Ala-Lys-Amide Scheme XI:

Acetyl-Cys(TP)-beta Ala-beta Ala-Lys-beta Ala-beta Ala-Lys-Amide

| mPEG5000-CM-HBA-NHS
| Phosphate Buffer pH = 7.5
| 6 h stirring/RT
↓

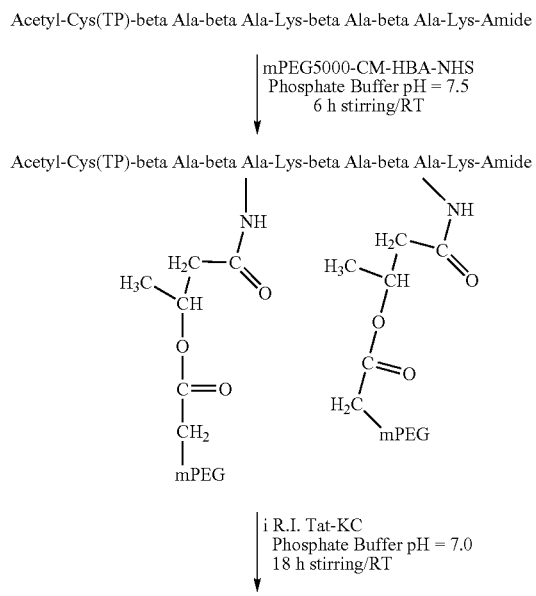

| i R.I. Tat-KC
| Phosphate Buffer pH = 7.0
| 18 h stirring/RT
↓

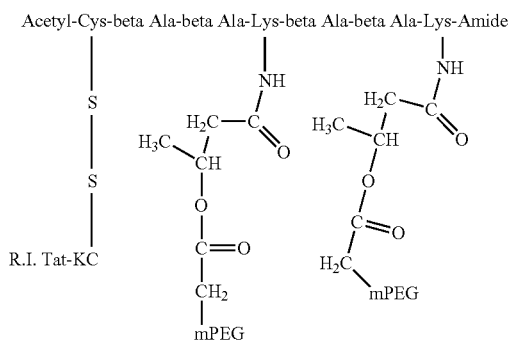

Scheme XII:

NH2-Cys(SH)-beta Ala-beta Ala-Lys-beta Ala-beta Ala-Lys-Amide

| mPEG5000-OPTE
| Phosphate Buffer pH = 6.0
| 24 h stirring/RT
↓ mPEG-Cys(SH)-beta Ala-beta Ala-Lys-beta Ala-beta Ala-Lys-Amide

| mPEG5000 NHS
| phosphate buffer pH = 7.5
| 6 h stirring, RT
↓

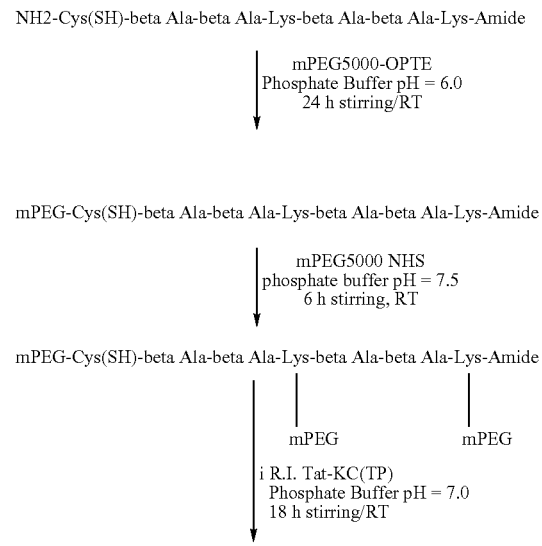

| i R.I. Tat-KC(TP)
| Phosphate Buffer pH = 7.0
| 18 h stirring/RT
↓

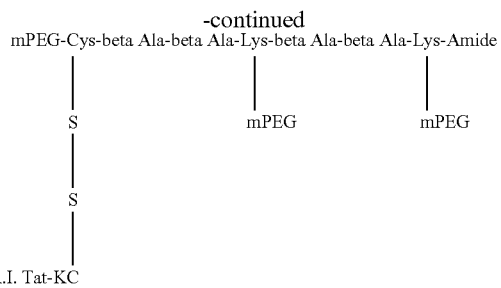

The invention described herein also includes various pharmaceutical dosage forms containing the macromolecular conjugate compositions of the present invention. The pharmaceutical dosage forms include those recognized conventionally, e.g. solutions, suspensions, emulsions, topical solutions, transdermal liquids and the like.

The pharmaceutical dosage forms may include one or more pharmaceutically acceptable excipients. Such materials are non-toxic to the recipients at the dosages and concentrations employed, and include diluents, solubilizers, suspending agents, penetration enhancers, solvents, emollients, thickeners, dispersants, transdermal delivery components, buffers, stabilizers, preservatives, and the like.

The macromolecular conjugate compositions of the present invention are suitable for applications where localized drug delivery is desired, as well as in situations where a systemic delivery is desired. The macromolecular conjugate compositions may be injected into the body of a patient in need thereof, by procedures that are essentially conventional and well known to those of ordinary skill in the art.

Physiologically stable conjugates are utilized when the effector or therapeutic agent is active in conjugated form or is otherwise intended to be delivered in conjugated form. In such circumstances the effector or therapeutic agent is defined as being irreversibly conjugated and the conjugation bonds are defined as being irreversible. Physiologically unstable conjugates are utilized when the effector or therapeutic agent is inactive in conjugated form or is otherwise intended to be delivered in non-conjugated form. In such circumstances the effector or therapeutic agent is defined as being reversibly conjugated and the conjugation bonds are defined as being reversible.

Reversible conjugates revert back to the active non-conjugated form of the effector or therapeutic agent. Physiologically unstable conjugates may employ conjugation linkages that are labile under physiological conditions, with or without enzyme catalysis. Examples of conjugate bonds that are physiologically labile without enzyme catalysis include disulfide bonds and ester bonds. Conjugates may be designed for enzyme catalyzed lability at the site of delivery by an enzyme that is native to the delivery site or administered to the delivery site before, during or after administration of the conjugate. The enzyme may be delivered with the conjugate or may already be present at the delivery site, and after conjugate administration an essential cofactor is delivered to reverse the conjugation.

Subjects in need of treatment, typically mammalian, using the macromolecular conjugate compositions of this invention, can be administered drug dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize. The macromolecular conjugate compositions of this invention may be prepared for storage under conditions suitable for the preservation of drug activity as well as maintaining the integrity of the polymers, and are typically suitable for storage at ambient or refrigerated temperatures.

Depending upon the particular compound selected, transdermal delivery may be an option, providing a relatively steady delivery of the therapeutic agent, which is preferred in some circumstances. Transdermal delivery typically involves the use of a compound in solution, with an alcoholic vehicle, optionally a penetration enhancer, such as a surfactant, and other optional ingredients. Matrix and reservoir type transdermal delivery systems are examples of suitable transdermal systems. Transdermal delivery differs from conventional topical treatment in that the dosage form delivers a systemic dose of the therapeutic agent to the patient.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each drug by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved. The release rate of the drug from the formulations of this invention is also varied within the routine skill in the art to determine an advantageous profile, depending on the therapeutic conditions to be treated.

A typical dosage might range from about 0.001 mg/k/g to about 1,000 mg/k/g, preferably from about 0.01 mg/k/g to about 100 mg/k/g, and more preferably from about 0.10 mg/k/g to about 20 mg/k/g. Advantageously, the compounds of this invention may be administered several times daily, and other dosage regimens may also be useful.

In practicing the methods of this invention, the macromolecular conjugate compositions may be used alone or in combination with other therapeutic or diagnostic agents. The compounds of this invention can be utilized in vivo, ordinarily in mammals such as primates such as humans, sheep, horses, cattle, pigs, dogs, cats, rats and mice, or in vitro.

The present invention is further illustrated by the following examples that teach those of ordinary skill in the art how to practice the invention. The following examples are merely illustrative of the invention and disclose various beneficial properties of certain embodiments of the invention. The following examples should not be construed as limiting the invention as claimed.

EXAMPLES

The following are examples of synthesis of conjugates considered to be representative of embodiments of the present invention or synthetic intermediates used in the preparation of embodiments of the present invention. All synthetic procedures are well known and are described in sufficient detail for someone skilled in the art of synthetic chemistry to prepare the desired product in each example. In general, the reagents are commercially available. Variations in reagent concentration, reaction time and temperature, and selection of particular protecting groups, activators and solvents can be made, as known in the art.

Example 1

Peptidic Carrier: Cys-Beta Ala-Lys (D-Amino Acids)

Water Soluble Polymer: Boc-PEG3400-NHS

Peptidic carrier—water soluble polymer was prepared as shown in Scheme IV. This polymer was purified by size exclusion chromatography using Sephadex LH-20 beads. The product was radiolabelled after the formation of the peptidic carrier-water soluble polymer. Before radiolabelling the product was confirmed using SEC-HPLC (UV detection) and MALDI-TOF/MS and after radiolabelling by using SEC-HPLC (Beta-ram detection). This product could further be linked to a therapeutic agent or an effector group after removal of Boc protection group. L-amino acids and different PEG sizes would give similar product.

Example 2

Peptidic Carrier: Cys-(Beta Ala-Lys)$_6$ (D-Amino Acids)

Water Soluble Polymer: Boc-PEG3400-NHS

Peptidic carrier—water soluble polymer was prepared as shown in Scheme V. This polymer was purified by size exclusion chromatography using Sephadex LH-60 beads. The product was radiolabelled after the formation of the peptidic carrier-water soluble polymer. Before radiolabelling the product was confirmed using SEC-HPLC (UV detection) and MALDI-TOF/MS and after radiolabelling by using SEC-HPLC (Beta-ram detection). This product could further be linked to a therapeutic agent or an effector group after removal of Boc protection group. L-amino acids and different PEG sizes would give similar product.

Example 3

Peptidic Carrier: Acetyl-Cys-(Beta Ala-Beta Ala-Lys)$_2$-Amide(SEQ ID NO: 3)

Water soluble polymer: VS-PEG5000-NHS

In this example, the peptidic carrier was synthesized by solid phase peptide synthesis (Fmoc chemistry). It was reacted with 3 molar excess of NHS-PEG(poly ethylene glycol)-VS [MW.about.5,000] in phosphate buffer 100 mM pH=7.5 to form the PEGylated peptidic carrier. The preparation method is shown in Scheme I. This macromolecule was purified from unreacted PEG by size exclusion chromatography and reacted in phosphate buffer 100 mM pH=8.0 with a modified form of the N-formyl peptide (f-MLFKC) (SEQ ID NO: 7). The result is a macromolecule with appended adjuvants (formyl peptide) via PEG. This reaction also resulted in formation of a formyl peptide moiety that is attached to the Cysteine residue of the peptide carrier. This attachment is reversible and was removed by DTT treatment. Note that the formyl peptide attachment to PEG is irreversible. This product was purified by dialysis, using a regenerated cellulose membrane (MWCO 3,000). The purified compound was reacted with Saquinavir-Cysteine-ester (see Gunaseelan et. al. 2004 for details) in order to form the compound. This macromolecule conjugate contains 2 copies of the effector (f-MLFKC) (SEQ ID NO: 7) and 1 copy therapeutic agent Saquinavir (SAQ).

Example 4

Peptidic Carrier: Acetyl-Cys-(Beta Ala-Beta Ala-Lys)$_4$-Amide(SEQ ID NO: 4)

Water Soluble Polymer: VS-PEG5000-NHS

The reaction conditions are identical to those in Example 3 and the preparation method is shown in Scheme II. The linkages, effector and therapeutic agent are identical to Example 3, however, in this example, the peptidic carrier has 4 moieties (Lysines) for attachment of NHS-PEG-VS. Thus the final product has 4 copies of effector (f-MLFKC) (SEQ ID NO: 7) per macromolecule conjugate. Also the PEG content/macromolecule is twice as much as Example 3.

Example 5

Peptidic Carrier (A)=Cys-(Beta Ala-Beta Ala-Lys)$_2$

Water Soluble Polymer (B)=VS-PEG5000-NHS

The reaction procedure corresponds to Scheme I. The cross-linker VS-VS (bis-vinylsulfone) is reacted at 30-fold molar excess of in 100 mM phosphate buffer pH=8.0. The huge molar excess is required in order to prevent dimmer peptide carrier formations. Then after purification (Size exclusion chromatography) a modified form of Tat (was added. In this example, the therapeutic agent (a modified form Tat, R.I. Tat-KC) has been linked via a non-reversible bond. In reaction Schemes II and III, the therapeutic agent was appended via a reversible linkage.

Example 6

Peptidic Carrier: -Cys-(Beta Ala-Beta Ala-Lys)$_2$(SEQ ID NO: 5)

Water Soluble Polymer: mPEG5000-OPSS

The peptidic carrier is reacted with m-PEG-OPSS (ortho-pyridyldisulfide-PEG, 5,000 MW) in phosphate buffer (100 mM, pH=7.5). The conjugate is purified by size exclusion chromatography. Then, reaction with a 10-fold molar excess of GMBS [N-(γ-maleimidobutyryloxy)succinimide ester] over the molar amount of the amines of the peptidic carrier-PEG conjugate is carried out for 2 hours. The product is precipitated in ether. Then a 5-fold molar excess of R.I. Tat-9KC peptide is added. The result is a PEGylated peptide carrier with non-reversible linkage of Tat and reversible linkage of PEG. The reaction procedure is depicted in Scheme VI.

Example 7

Peptidic Carrier: Acetyl-Cys-(Beta Ala-Beta Ala-Lys)$_2$-Amide(SEQ ID NO: 3)

Water Soluble Polymer: PEG 5000-(Mal)2

The peptidic carrier is reacted with 5-fold molar excess of PEG(maliamide)$_2$, overnight at room temperature in phosphate buffer (100 mM) pH=7.5. Then the unreacted PEG-(Mal)2 was reacted with 10 fold molar excess of DTT in phosphate suffer pH for 6 hours. Then the product is dialyzed against water using a regenerated cellulose membrane (MWCO 3,000 Da). The product is reacted with 5-fold molar excess of NHS-PEG 5KDa-VS in phosphate buffer pH=7.5 in room temperature for 16 hours. Then it was reacted with 20-fold molar excess of R.I. CK-Tat in phosphate buffer (100 mM, pH=7.0) for 16 hours. The product is purified by size exclusion chromatography. The therapeutic agent R.I. Tat9-KC is attached via PEG by non-reversible linkage. The macromolucle consists of 2 subunits of peptidic carrier (attached via PEG 5000 Da). There are 4 moles of the therapeutic agent (Tat) per mole of the macromolecule. The reaction procedure is depicted in Scheme VII.

Example 8

Peptidic Carrier: Acetyl-Cys-(Beta Ala-Beta Ala-Lys)$_2$-Amide(SEQ ID NO: 3)

Water Soluble Polymer: mPEG5000-(OPSS)$_2$

The peptidic carrier is reacted with 5-fold molar excess of mPEG(OPSS)$_2$, overnight at room temperature in phosphate buffer (100 mM) pH=7.5. Then the product is reacted with 5-fold molar excess of NHS-PEG 5KDa-VS in phosphate buffer pH=7.5 in room temperature for 16 hours. Finally it was reacted with 20-fold molar excess of R.I. CK-Tat in phosphate buffer (100 mM, pH=7.0) for 16 hours. The product is purified from unreacted mPEG(OPPS)$_2$, VS-PEG5000-NHS and R.I. Tat-KC by size exclusion chromatography. This example is nearly identical to the previous example, except that the peptidic carriers are linked via reversible disulfide bonds. Thus the pharmacokentics and bioavailability of this macromolecule could differ from that of Example 7. The reaction procedure is depicted in Scheme VIII.

Example 9

Peptidic Carrier: Acetyl-Cys-(Beta Ala-Beta Ala-Lys)$_2$-Amide(SEQ ID NO: 3)

Water Soluble Polymer: Amino-PEG 10,000 4-arm and VS-PEG 5,000 NHS

Amino PEG 10,000, 4-arm [PEG 10,000-(NH$_2$)$_4$ is reacted with 5-fold molar excess of GMBS to the amine moieties in PEG. The reaction condition is; DCM:DIEA (99:1) in room temperature for 6 hours. The product [PEG 10,000-Mal)$_4$] is dialyzed against water, using regenerated cellulose membrane (MWCO 3,000). The purified product is reacted with 3 molar excess of the peptidic carrier. The peptidic carrier-PEG conjugate is purified from the unreacted peptidic carrier by dialysis as above. Then VS-PEG-NHS and R.I. Tat-KC was appended to the conjugate as described in example 7. In this example, 8 copies of the therapeutic agent is covalently linked to peptidic carriers. There are 4 peptidic carriers that are attached to a central PEG polymer (4-arm PEG) via non-releasable peptide linkages. The reaction procedure is depicted in Scheme IX.

Example 10

Peptidic Carrier: Acetyl-Cys-(Beta Ala-Beta Ala-Lys)$_2$-Amide(SEQ ID NO: 3)

Water Soluble Polymer: Amino-PEG 10,000 4-arm and VS-PEG 5,000 NHS

This example is identical to the previous example except that the linkage of the peptidic carriers to the central 4-arm PEG moiety is by a reversible manner. Scheme 10 depicts the synthesis and structure of the macromolecule.

Example 11

Peptide Carrier: Acetyl-Cys-(Beta Ala-Beta Ala-Lys)$_2$-Amide(SEQ ID NO: 3)
Water Soluble Polymer: mPEG5000-CM-HBA-NHS Scheme 11 depicts the reaction procedure. In this example, a degradable ester form of NHS is used. The ester between carboxymethyl (CM) and the 3-hydroxybutanoic acid (HBA) provides the conjugate degradability by hydrolysis in aqueous conditions, providing for controllable hydrolytic release of the bound molecule.

Example 12

In this example, the peptidic carrier is not acetylated at the N-terminus, unlike all other example. Thus the N-terminus cysteine is reactive toward O-pyridylthioester (OPTE) PEG. This adds an additional PEG linkage for the carrier. The requirement is that the N-terminus be cysteine with an unhindered thiol. All other PEGylation and conjugations are performed as described before. Thus the N-terminus of Cysteine moiety is used as an additional site of PEGylation. Scheme 12 depicts the reaction procedure.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

---

What is claimed is:

1. A monodisperse macromolecular conjugate composition for in-vivo delivery of a therapeutic agent comprising a peptidic carrier reversibly or irreversibly conjugated with: (a) one or more effectors and (b) one or more therapeutic agents, wherein said peptidic carrier comprises at least two different orthogonal pendant reactive groups each for specific attachment of a predetermined effector or therapeutic agent and at least one effector or therapeutic agent is attached to at least one of said pendant reactive groups on said peptidic carrier via a water-soluble polymer, and wherein said peptidic carrier comprises an amino acid sequence selected from the group consisting of: Cys-beta Ala-Lys (SEQ ID NO: 1); Cys-(beta Ala-Lys)$_6$ (SEQ ID NO: 2); Acetyl-Cys-(beta Ala-beta Ala-Lys)$_2$-Amide (SEQ ID NO: 3);

Acetyl-Cys-(beta Ala-(beta Ala-Lys)$_4$-Amide (SEQ ID NO: 4); and Cys-(beta Ala-beta Ala-Lys)$_2$ (SEQ ID NO: 5).

2. The composition of claim 1, wherein said peptidic carrier comprises 1 to 50 amino acid subunits, amino acid-like subunits, or a combination thereof.

3. The composition of claim 2, wherein said peptidic carrier comprises 2 to 20 amino acid subunits, amino acid-like subunits, or a combination thereof.

4. The composition of claim 3, wherein said peptidic carrier comprises 3 to 8 amino acid subunits, amino acid-like subunits, or a combination thereof.

5. The composition of claim 1, wherein each pendant reactive group is independently selected from the group consisting of a primary amine, a carboxylic acid, an alcohol, a phenol, a thiol, a hydrazide, a hydrazone, a ketone, an oxime, and an aldehyde.

6. The composition of claim 1, wherein at least one therapeutic agent or effector is attached by reversible bonds to the peptidic carrier or to a water soluble polymer conjugated to said peptidic carrier.

7. The composition of claim 6, wherein said reversible bond is a disulfide or ester bond.

8. The composition of claim 5, wherein said peptidic carrier comprises one or more pendant groups formed thereon independently selected from the group consisting of a thiol, a primary amine, a carboxylic acid, an alcohol, and a phenol and said effector or therapeutic agent is conjugated thereto by means of a group reactive therewith on said effector or therapeutic agent.

9. The composition of claim 5, wherein said peptidic carrier comprises one or more pendant groups formed thereon independently selected from the group consisting of a thiol, a primary amine, a carboxylic acid, an alcohol, and a phenol and said effector or therapeutic agent is conjugated thereto by means of a water-soluble polymer on said effector or therapeutic agent.

10. The composition of claim 1 comprising 2 to 5 different orthogonal reactive groups attached to the central peptidic core.

11. The composition of claim 5, wherein there are 1 to 24 copies of each reactive group.

12. The composition of claim 11, wherein there are 3 to 8 copies of each reactive group.

13. The composition of claim 1, wherein said water-soluble polymer comprises poly(ethylene glycol).

14. The composition of claim 13, wherein said poly(ethylene glycol) is branched.

15. The composition of claim 13, wherein said poly(ethylene glycol) has a molecular weight of from 1,000 to 100,000 daltons.

16. The composition of claim 15, wherein said poly(ethylene glycol) has a molecular weight of from 2,000 to 5,000 daltons.

17. The composition of claim 5, wherein said reactive group is chemoselective with a reactive group attached to said water soluble polymer prior to conjugation.

18. The composition of claim 5, wherein said reactive group is chemoselective with a reactive group attached to said effector prior to conjugation.

19. The composition of claim 1 comprising up to 10 different effectors.

20. The composition of claim 19 comprising from 1 to 50 copies of each effector.

21. The composition of claim 20 comprising from 1 to 4 copies of each effector.

22. The composition of claim 1 comprising up to 10 different therapeutic agents.

23. The composition of claim 22 comprising from 1 to 50 copies of each therapeutic agent.

24. The composition of claim 23 comprising from 1 to 4 copies of each therapeutic agent.

25. The composition of claim 1, wherein said effector is selected from the group consisting of ligands or substrates for receptors, membrane influx or efflux transporters, and enzymes; tissue- and cell-specific targeting groups; permeability enhancers, and modifiers of cell-machinery, cell-signaling or cell-disposition.

26. The composition of claim 1, wherein said peptidic carrier comprises at least one first reactive group selected from the group consisting of thiols, primary amines, carboxylic acids, alcohols, phenols, hydrazides, hydrazones, ketones, oximes, and aldehydes, to which a first therapeutic agent or first effector is conjugated; and at least one second reactive group orthogonal to said at least one first reactive group and selected from the group consisting of list thiols, primary amines, carboxylic acids, alcohols, phenols, hydrazides, hydrazones, ketones, oximes, and aldehydes to which a second therapeutic agent or second effector is conjugated.

27. The composition of claim 26, wherein said first therapeutic agent is an anti-retroviral therapeutic agent.

28. The composition of claim 26, wherein said first effector is a cell surface receptor ligand.

29. The composition of claim 28, wherein said first effector is fMLF.

30. The composition of claim 28, wherein said first effector is mannose.

31. The composition of claim 28, wherein said first effector is folate.

32. The composition of claim 26, wherein said second therapeutic agent is an antineoplastic therapeutic agent.

33. The composition of claim 32, wherein said second therapeutic agent is campothecin.

34. The composition of claim 32, wherein said second therapeutic agent is paclitaxel.

35. The composition of claim 32, wherein said second therapeutic agent is doxorubicin.

36. The composition of claim 26, wherein said second effector is a cell penetrating peptide.

37. The composition of claim 36, wherein said second effector is R.I.Tat9-KC.

38. A method for preparing a monodisperse macromolecular conjugate composition for in-vivo delivery of a therapeutic agent, wherein the macromolecular conjugate comprises a peptidic carrier conjugated with one or more effectors and one or more therapeutic agents, wherein the method comprises the steps of:
   (a) providing a peptidic carrier comprising first and second orthogonal pendant reactive groups, said first orthogonal pendant reactive group for specific attachment of a predetermined effector and said second orthogonal pendant reactive group for specific attachment of a predetermined therapeutic agent, wherein said peptidic carrier is according to claim 1;
   (b) attaching said effector to said peptidic carrier by means of a water-soluble polymer such that each copy of an effector is attached to the same reactive groups on each peptidic carrier in the composition; and
   (c) attaching said therapeutic agent to said peptidic carrier by means of a water-soluble polymer such that each copy of a therapeutic agent is attached to the same reactive groups on each peptidic carrier in the composition.

39. A monodisperse macromolecular conjugate composition comprising a peptidic carrier, wherein said peptidic carrier comprises at least two different orthogonal pendant reactive groups, wherein at least one of said pendant reactive groups on said peptidic carrier is attached to a water-soluble polymer, and wherein said peptidic carrier comprises an amino acid sequence selected from the group consisting of: Cys-beta Ala-Lys (SEQ ID NO: 1); Cys-(betaAla-Lys)$_6$(SEQ ID NO: 2); Acetyl-Cys-(beta Ala-beta Ala-Lys)$_2$-Amide (SEQ ID NO: 3); Acetyl-Cys-(beta Ala-(beta Ala-Lys)$_4$-Amide (SEQ ID NO: 4); and Cys-(beta Ala-beta Ala-Lys)$_2$ (SEQ ID NO: 5).

40. A method for treating a condition linked to a viral disorder, comprising administering to a patient in need thereof an effective amount of a composition according to claim 1, wherein said therapeutic agent is an anti-infective agent having anti-viral activity and said effector aids the anti-viral action of said therapeutic agent.

41. A method for treating a condition linked to a microbial disorder, comprising administering to a patient in need thereof an effective amount of a composition according to claim 1, wherein said therapeutic agent is an anti-infective agent having anti-microbial activity and said effector aids the anti-microbial action of said therapeutic agent.

42. A method for treating a condition linked to a hyperproliferative disorder, comprising administering to a patient in need thereof an effective amount of a composition according to claim 1, wherein said therapeutic agent is an anti-neoplastic agent having anti-neoplastic activity and said effector aids the anti-neoplastic action of said therapeutic agent.

* * * * *